United States Patent
Ruszczak et al.

(10) Patent No.: US 6,855,860 B2
(45) Date of Patent: Feb. 15, 2005

(54) COMPOSITE DRESSINGS FOR THE TREATMENT OF WOUNDS

(75) Inventors: Zbigniew Ruszczak, Munich (DE); Robert Mehrl, Langquald (DE); Johann Jeckle, Riedenburg (DE)

(73) Assignee: Syntagoll AG, Herisau (CH)

( * ) Notice: Subject to any disclaimer, the term of this patent is extended or adjusted under 35 U.S.C. 154(b) by 121 days.

(21) Appl. No.: 10/231,667

(22) Filed: Aug. 30, 2002

(65) Prior Publication Data

US 2003/0078532 A1 Apr. 24, 2003

Related U.S. Application Data

(63) Continuation-in-part of application No. PCT/EP00/01905, filed on Mar. 3, 2000.

(51) Int. Cl.$^7$ ............................ A61F 13/00; A61L 15/00
(52) U.S. Cl. ............................ 602/48; 602/46; 424/445
(58) Field of Search .................. 424/443–449; 604/304–308; 602/41–59

(56) References Cited

U.S. PATENT DOCUMENTS

| | | | |
|---|---|---|---|
| 3,900,027 A | * 8/1975 | Keedwell | 604/307 |
| 4,060,081 A | 11/1977 | Yannas et al. | 128/156 |
| 4,407,787 A | 10/1983 | Stemberger | 424/28 |
| 4,578,067 A | 3/1986 | Cruz, Jr. | 604/368 |
| 4,925,924 A | 5/1990 | Silver et al. | 530/356 |
| 4,965,203 A | * 10/1990 | Silbering et al. | 435/188 |
| 5,290,552 A | * 3/1994 | Sierra et al. | 424/94.64 |
| 5,556,391 A | * 9/1996 | Cercone et al. | 604/369 |
| 5,709,934 A | * 1/1998 | Bell et al. | 428/305.5 |
| 2003/0021827 A1 | * 1/2003 | Malaviya et al. | 424/424 |

FOREIGN PATENT DOCUMENTS

EP 05999589 2/1999 ........... A61F/13/00

* cited by examiner

*Primary Examiner*—Kim M. Lewis
(74) *Attorney, Agent, or Firm*—Fulbright & Jaworski L.L.P.

(57) ABSTRACT

Non-occlusive composite wound dressings that comprises a material polymer wound-healing layer comprised of isolated polymer fibers, and a synthetic polymer foam layer having at least one surface physically adhered to the natural layer by the physical interlocking of the polymer fibers with the surface. Also, a process for the preparation of a non-occlusive composite wound dressing comprising contacting a synthetic polymer foam porous surface with a solution and/or suspension of natural polymer fibers in a medium, and removing the medium from the fibers under conditions that result in the fibers penetrating into pores of the surface and that form a dried composite of the polymer foam adhered physically to a layer comprising natural polymer fiber.

4 Claims, No Drawings

US 6,855,860 B2

COMPOSITE DRESSINGS FOR THE TREATMENT OF WOUNDS

This application is a continuation-in-part of PCT Application PCT/EP00/01905 designating the US and filed Mar. 3, 2000.

FIELD OF THE INVENTION

The present invention relates to the field of medical devices useful for wound treatment and methods for the treatment of wounds. In particular, the present invention relates to the field of relatively deep wound treatment, as opposed to the treatment of superficial scrapes and bruises. The wounds of present concern involve not only the upper layer of skin or epidermis, but also the middle and deepest layers of skin such as the dermis. Such injuries occur, for example, in second- and third-degree burns, in a variety of different acute and/or chronic skin disorders, such as leg ulcers (ulcera crurum) having diverse origin (arterial and/or venous and/or neuropathic and/or trophic) as well as in pressure ulcers or decubital ulcers.

The present invention may also find use in medical treatments where for a variety of reasons the temporary stabilization of acute and fresh wounds of non-surgical and/or surgical origin is desirable. Such situations may arise due to the treatment procedure, time, anatomical localization or emergency, where the wound cannot be closed by standard surgical procedures or requires a second surgical intervention.

Reported Developments

Bandages of woven, webbed and non-woven mats of natural and synthetic fibrous materials are known to treat wounds as described above. For example, the present applicants market sponges prepared from isolated collagen fiber, such as animal-derived collagen, for example, COLLATAMP® products. The patent literature further discloses the preparation of membranes, sometimes referred to as fascia or fleeces, and and/or films of natural polymers, such as collagen.

European Patent No. EP0069260 describes collagen inserts prepared from a fascia of collagen sheet wound into a rod for insertion into the body.

U.S. Pat. No. 4,407,787 discloses a tissue adherent collagenous dressing including a second adherent polymer such as fibrinogen, and optionally a medicament.

European Patent No. EP0090997 discloses a dry, fleecy or spongy tissue-adherent flat collagenous dressing made of collagen and fibrinogen, characterized in that the dressing is made in layers by freeze-drying a collagen/fibrinogen combination and contains a collagen layer, and which has on at least one surface a fibrinogen layer which is anchored in the collagen.

U.S. Pat. No. 4,578,067 discloses a hemostatic-adhesive, collagen dressing for severed biological surfaces, comprising a dry-laid, non-woven, self-supporting web formed from a mass of hemostatic-adhesive, collagen fibers.

It is also known that natural polymers such as collagen may be combined with synthetic polymers such as silicone to form wound dressings.

U.S. Pat. No. 4,060,081 describes the preparation of multilayer membranes useful as dressings for the treatment of burns, cuts, lacerations, abrasions, and other such conditions that involve injury or destruction of skin. The multi-layer composite consists of a non-biodegradable cross linked collagen mucopolysaccharide sponge layer, and a second non-porous synthetic polymer (such as silicone) layer, both layers being chemically bonded to each other. This product is commercially available as Integra® Artificial Skin (Integra® Life Sciences, USA), which acts as an occlusive dressing because the silicone layer of such product is not highly air-and water-permeable. The '081 patent discloses that during manufacture, the thin silicone layer is applied to the collagen sponge as a partially polymerized silicone pre-polymer that is allowed to fully polymerize in contact with, and thereby chemically bond to, the collagen sponge layer. The polymerization process may takes days to complete and during polymerization undesirable chemicals, such as acetic acid, penetrate into the natural collagen sponge layer. The disclosed dressings incorporate chemically modified collagen composite materials, that tend to provoke an immune response in the absence of additional immunosuppressive agents, and the layers of the composite are so tightly chemically bonded that removal of the dressing is likely to cause physical injury to the healing wound tissue. The '081 patent discloses further that the product requires special handling and sterilization prior to use. The commercial embodiment, Integra® Artificial Skin wound dressing, must be stored in a special container with liquid preservative, in particular, glycerol, which must be removed by washing prior to use, and is time-consuming for both surgeon and medical staff.

European Patent Publication EP-A-0599589 discloses a wound dressing comprising an absorbent layer, such as a polyurethane foam, a wound-contact layer, which is preferably collagen containing glycosaminogtycans, a molecular filtration membrane disposed between the two layers. The '589 publication discloses that the wound contact layer is attached to the porous synthetic molecular filtration layer while the synthetic foam layer is attached to the membrane layer through the use of a separate adhesive layer. The '589 publication neither discloses nor suggests how the synthetic foam layer may be attached to the wound contacting polymeric layer.

The present invention answers the need for a composite dressing product that is easy to manufacture, and capable of manufacture without using any adhesives, cross-linking or polymerization catalysts or prepolymers, thereby reducing, if not totally eliminating, the risk of diffusion of biologically incompatible or toxic chemical products into the wound-contacting layers of the dressing. Furthermore, the present invention provides for a composite wound dressing that is non-occlusive, permitting water vapor, wound fluid and air to penetrate the composite dressing; is easy to apply to a wound; and, is easy to separate its overlying protecting layer from the wound-healing layer in contact with the wound after a convenient period of time without adversely affecting the healing process.

The present invention is ready to use and maintains its composite integrity in its package and during application to the wound site. Furthermore, the present composite dressing may be taken directly from the packaging and applied directly to the wound surface without additional preparation or pre-treatment.

The various aspects, uses, methods and elements of the present invention are more particularly described in the following sections.

SUMMARY OF THE INVENTION

The present invention relates to a non-occlusive composite wound dressing comprising (1) a natural polymer wound-healing layer comprised of isolated polymer fibers, and (2) a synthetic polymer foam layer having at least one pore-containing surface contacting said natural layer and physically adhered to said natural layer by the physical interlocking of said polymer fibers with said pore-containing surface.

Another aspect of the present invention is a process for the preparation of a non-occlusive composite wound dressing comprising:

(a) contacting a synthetic polymer foam porous surface with a solution and/or suspension of natural polymer fibers in a medium; and (b) removing said medium from said fibers under conditions that result in said fibers penetrating into pores of said surface and that form a dried composite of said synthetic polymer foam adhered physically to a layer comprising natural polymer fiber.

A further aspect of the present invention is the non-occlusive composite wound dressing produced in accordance with the aforesaid process.

The present invention is more full described and exemplified in the following detailed description.

DETAILED DESCRIPTION

The following terms are intended to have the meanings provided herein below:

The term "antibiotic" as used herein means a substance produced synthetically or isolated from natural sources that selectively inhibits the growth of a microorganism.

The term "biocompatible" as used herein means the ability of a material to pass the biocompatibility tests set forth in International Standards Organization (ISO) Standard No. 10993 and/or the U.S. Pharmacopoeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." These tests assay as to a material's toxicity, infectivity, pyrogenicity, irritation potential, reactivity, hemolytic activity, carcinogenicity, and/or immunogenicity. A biocompatible composite, or polymer comprising a layer thereof, when introduced into a majority of patients will not cause an adverse reaction or response. In addition, it is contemplated that biocompatibility can be effected by other contaminants such as prions, surfactants, oligonucleotides, and other biocompatibility effecting agents or contaminants.

The term "contaminant" as used herein means an unwanted substance on, attached to, or within a material, such a layer of the present composite. This includes, but is not limited to bioburden, endotoxins, processing agents such as antimicrobial agents, blood, blood components, viruses, DNA, RNA, spores, fragments of unwanted tissue layers, cellular debris, and mucosa.

The term "bioinert" as used in relation to a material means a material that does not interact with biological systems. A "bio-inert" material is non-reactive with the components of blood, and tissues, including the immunological and coagulation systems. Bioinert substances neither initiate coagulation nor raise an immunological response in host tissue, and the chemical make-up of such substances is not altered while in contact with such biological systems.

The term "cells" as used herein means a single unit biological organism that may be eukaryotic or prokaryotic. The eukaryotic cell family includes yeasts and animal cells, including mammalian and human cells. Cells that may be useful in conjunction with the present invention include cells that may be obtained from a patient, or a matched donor, and used to seed a wound site. Such seeding would be used in an effort to repopulate the wound area with specialized cells, such as dermal, epidermal, epithelial, muscle or other cells, or alternatively to provide cells those stimulates or are involved in providing immunological protection to fight off infectious organisms. Such cells may be isolated and extracted from the patient, and/or genetically reengineered to produce a host of cytokines, antibodies, or other growth factors to aid in the wound healing process.

The term "cell extract" as used herein means a material derived from whole cells, but comprising less than whole cells, such as a protein extract or DNA extract.

The term "composite" as used herein means a solid material which is composed of two or more substances having different physical characteristics and in which each substance retains its identity while contributing desirable properties to the whole.

The term "cytokine" as used herein means a small protein released by cells that has a specific effect on the interactions between cells, on communications between cells or on the behavior of cells. The cytokines includes the interleukins, lymphokines, and cell signal molecules, such as tumor necrosis factor and the interferons, which trigger inflammation and respond to infections. Many cytokines are produced by recombinant technology and are presently available for use in research as well as by prescription in human and animal subjects.

The term "foam" as used herein means a solid material, throughout which are distributed voids, pores or cells, which are at least partially open and function to interconnect the voids throughout the material. Foam materials may be produced from a polymerization mixture containing gas-generating agents or through which gas is pumped during the polymer solidification process.

The term "growth factor" as used herein means a substance (as a vitamin $B_{12}$ or an interleukin) that promotes growth and especially cellular growth. Examples of growth factors include, but are not limited to, epidermal growth factor, which is a polypeptide hormone that stimulates cell proliferation, nerve growth factor, which is a protein that promotes development of the sensory and sympathetic nervous systems and is required for maintenance of sympathetic neurons, vascular endothelial growth factors, which are a family of proteins that stimulate angiogenesis by promoting the growth of vascular endothelial cells, and the like.

The term "medicament" as used herein means a substance used in medical therapy, such as the therapeutically effective active ingredient in a pharmaceutical.

The term "membrane" as used herein means a thin soft pliable sheet or layer.

The term "natural polymer" as used herein means a polymer that is found in nature and that may be derived from natural sources or produced synthetically. More particularly, the natural polymer means a polymer comprising repeating subunits of small organic molecules found in biological systems including microorganisms, plants, and animals. Exemplary subunit molecules include the groups of molecules known as the nucleotides, amino acids, and saccharide molecules. Polymers containing these small molecules comprise the polynucleic acids, such as the polyribonucleic acids and the polydeoxyribonucleic acids, the polypeptides, such as the proteins such as the structural proteins collagen and keratin, and small polypeptides comprising certain hormones and other signaling molecules, and polysaccharides, such as the cellulose and alginic acid family of molecules, respectively.

The term "non-occlusive" as used herein means not, or not tending to, close, shut-up, stop up, obstruct, or prevent the passage.

The term "pore" as used herein means a small interstice admitting the absorption or passage of liquid. "Porous" means a material containing pores.

The term "reconstituted" as used herein describes a solid material that has its origin in a solid source or form such as a solid matrix, that has been disrupted by chemical, physical or biological processes, that may have been dispersed or dissolved in a liquid medium, and that has been reformed, or restructured, into a further solid form having a structure that is modified physically and/or chemically relative to the original solid form of the material.

The term "sponge" as used herein means an elastic porous mass of interlacing fibers that is able when wetted to absorb water.

The term "synthetic polymer" as used herein means a polymer comprising repeating subunits of small organic molecules that are not found in natural biological systems. Exemplary subunit molecules include the urethanes, esters, ethers, silicones, vinyl alcohols, halovinyl alcohols, amides, fluorinated alkanes, styrene, and halogenated arylenes.

The non-occlusive composite wound dressing of the present invention comprises a natural polymer wound-healing layer, and a synthetic polymer foam layer having at least one pore-containing surface contacting said natural layer and physically adhered to said natural layer by the physical interlocking of said polymer fibers with said pore-containing surface. The natural polymer is comprised of isolated polymer fibers that are biocompatible and biodegradable. Such fibers may originate with plant and/or animal sources or be manufactured using recombinant technology. The present invention uses fibers that are preferably isolated from their original environment to exclude other materials such as other biological materials that exist naturally along with such fibers. Alternatively, such fibers are isolated preferably from the recombinant fermentation broth (and extracts therefrom), in which recombinant fibers are produced. The isolated fibers are preferably used for the present composite and preferably comprise the form of a restructured layer of isolated fibers. The natural polymer layer of the composite stimulates wound healing, provides a natural matrix for the formation of a granulation tissue, accelerates angiogenesis and neo-vascularization and prevents non-physiological scarring and cicatrizing, respectively.

According to a preferred embodiment of the present invention, the natural polymer fiber material comprises collagen. More than 20 different types of collagen are known, most of which are structurally important for the composition of extracellular matrices and for the normal function of tissues and organs. The more preferred collagens used for the present invention are known as Type-1, Type-11, Type-III, Tape-VII, Type-IX, and a mixtures of at least two of such types. This collagen may be a natural (native) or/and re-natured collagen obtained from both animal or human tissue, recombinant, or transgenic collagen that is obtained by genetic engineering and that is analogous or similar to animal or human collagen.

Collagen fibers are preferably isolated from the skins and/or tendons of cattle and/or calves and/or horses by known techniques, and the isolated collagen fibers used in the form of a dispersion to form the layer of the present composite. The more preferred collagen fibers are helical; more specifically triple helical in nature. To minimize its potential antigenic properties, the collagen fibers more preferably are treated with enzymes to remove non-helical parts of the protein, which is the protein material known as atelocollagen. A most preferred non-occlusive dressing according to present invention comprises natural polymer fibers consisting essentially of helical collagen fibers.

A most preferred collagen material for use in the present invention is the known and commercially available natural collagen polymer used in products such as COLLATAMP^-Fascie (film) and/or COLLATAMP® (sponge). These isolated collagen fiber materials are non-antigenic, at least partially porous, and gas and water vapor permeable.

The natural polymer layer of the composite optionally includes additional wound-healing agents such as polysaccharides, glycosaminogtycans, proteins, such as cytokines and growth factors, cells or cell extracts, and medicaments, such as antibiotics. Exemplary antibiotics include but are not limited to gentamycin, tetracycline, doxycycline, teicoplanin, quinoline antibiotics including the fluroquinolones, vancomycin, synercid®, penicillin derivatives and the cephlosporins.

One or more protein agents may be incorporated to promote granulation tissue deposition, angiogenesis, re-epithelialization, and fibroplasia. Additionally, these and other factors are known to be effective immunomodulators (either locally or systemically), hematopoietic modulators, osteoinductive agents, and oncostatic agents (e.g., TGF-beta has been shown to exhibit all of these activities). The bioactive additives or protein factors used herein may be native or synthetic (recombinant), and may be of human or other mammalian type. Human FGF (including both acidic or basic forms), PDGF, and TGF-beta are preferred. Methods for isolating FGF from native sources (e.g., pituitary, brain tissue) are described in Bohlen et al, Proc Nat Acad Sci USA, (1984) 81:5364, and methods for isolating PDGF from platelets are described by Rainer et al, J Biol Chem (1982) 257:5154. Kelly et al, EMBO J (1985) 4:3399 discloses procedures for making recombinant forms of PDGF. Methods for isolating TGF-beta from human sources (platelets and placenta) are described by Frolik et al in EPO 128,849 (Dec. 19, 1984). Methods for isolating TGF-beta and TGF-beta2 from bovine sources are described by Seyedin et al, EPO 169,016 (Jan. 22, 1986), and U.S. Ser. No. 129,864, incorporated herein by reference. Other exemplary agents include, without limitation, transforming growth factor-alpha, beta-thromboglobulin, insulin-like growth factors (IGFs), tumor necrosis factors (TNFs), interleukins (e.g., IL-1, IL-2, etc.), colony stimulating factors (e.g., G-CSF; GM-CSF, erythropoietin, etc.), nerve growth factor (NGF), and interferons (e.g., IFN-alpha, IFN-beta, IFN-gamma, etc.). Synthetic analogs of the factors, including small molecular weight domains, may be used provided they exhibit substantially the same type of activity as the native molecule. Such analogs are intended to be within the scope of the term "wound healing agent," as well as within the specific terms used to denote particular factors, e.g., "FGF," "PDGF," and "TGF-beta." Such analogs may be made by conventional genetic engineering techniques, such as via expression of synthetic genes or by expression of genes altered by site-specific mutagenesis. Factors, such as with PDGF, may be incorporated into the native polymer layer in its native form (i.e., in platelets), or as crude or partially purified releasates or extracts. Alternatively, the factors may be incorporated in a substantially pure form free of significant amounts of other contaminating materials.

Such additional wound healing agents are included in the natural polymer layer in therapeutically effective local concentration amounts. The amount of the wound healing agent included in the composite of the present invention will depend upon the particular agent involved, its specific activity, the type of condition to be treated, the age and condition of the subject, the severity of the condition and intended therapeutic effect. For example, it may be necessary to administer a higher dosage of a factor when using the composite to treat a wound resulting from surgical excision of a tumor, than when simply promoting the healing of a wound (e.g., due to trauma or surgical procedure). In most instances, the protein factor(s) will be present in amounts in the range of about 3 ng/mg to 30 ug/mg based on weight of collagen. Antibiotic agents, such as gentamycin, are present in amounts that range from about 100 microgram/cm$^3$ to about $1 \times 10^4$ microgram/cm$^3$.

An "immunomodulatory amount" of agent is an amount of a particular agent sufficient to show a demonstrable effect on the subject's immune system. Typically, immunomodulation is employed to suppress the immune system, e.g., following an organ transplant, or for treatment of autoimmune disease (e.g., lupus, autoimmune arthritis, autoimmune diabetes, etc.). For example, when transplanting an organ one could line the site with the matrix of the invention impregnated with an immunomodulatory amount of an immunosuppressive biological growth factor to help suppress rejection of the transplanted organ by the immune system. Alternatively, immunomodulation may enhance the immune system, for example, in the treatment of cancer or serious infection (e.g., by administration of TNF, IFNs, etc.).

An "oncostatically effective amount" is that amount of growth factor that is capable of inhibiting tumor cell growth in a subject having tumor cells sensitive to the selected agent. For example, many non-myeloid carcinomas are sensitive to treatment with TGF-beta, particularly TGF-beta2.

A "hematopoietically modulatory amount" is that amount of growth factor that enhances or inhibits the production and/or maturation of blood cells. For example, erythropoietin is known to exhibit an enhancing activity at known dosages, while TGF-beta exhibits an inhibitory effect.

An "osteoinductive amount" of a biological growth factor is that amount which causes or contributes to a measurable increase in bone growth, or rate of bone growth.

The wound healing agents are preferably added to the collagen dispersion prior to the removal of the medium by evaporation or flash freezing and lypholisation.

A most preferred aspect of the present invention relates to the non-occlusive nature of the composite dressing. Both the biological and the synthetic polymer layers of the composite dressing have an open-pore or at least a partially open pore structure, thereby permitting both wound fluid and air to penetrate both component layers and to exchange fluids, nutrients and gases. Thus, according to the invention, due to the absence of occlusion, the final composite product enhances the wound healing process.

A preferred embodiment of the non-occlusive composite dressing according to the present invention comprises a natural polymer layer that is in the form of a porous collagen sponge.

Another preferred embodiment of the non-occlusive composite dressing according to the present invention comprises a natural polymer layer that is in the form of a transparent membrane.

In either of the aforesaid preferred embodiments, the composite is designed such that no additional chemical cross-linking procedure is necessary retain the porous nature of the sponge form or semi-porous structure of the membrane form of the natural polymer layer.

The present inventive dressing comprises the aforesaid synthetic polymer foam layer. Preferred synthetic polymer foams are at least a partially air- and water vapor-permeable, biocompatible and may be either biodegradable or non-biodegradable.

A preferred composite dressing comprises a synthetic foam layer comprises a non-biodegradable, and bio-inert polymer that when combined with the aforesaid natural polymer is fully polymerized. Exemplary preferred non-biodegradable synthetic polymers include but are not limited to silicone, polyurethane, and polyvinyl alcohol.

A most preferred non-biodegradable synthetic polymer is a silicone polymer, most preferably, silicone elastomer foam.

Another preferred composite dressing comprises a synthetic foam layer comprises a biodegradable, and bio-inert polymer that when combined with the aforesaid natural polymer is fully polymerized. Exemplary preferred biodegradable synthetic polymers include but are not limited to hyaluronic acid, polylactic acid, polylactides, or copolymers thereof.

Open- and/or mixed-pore foams of synthetic polymers are known, and include for example, foams of polyvinyl alcohol, polyurethane or, preferably, silicone elastomer. These foams are available in various different designs making them suitable for wound treatment. For example such foams may be available as perforated sheets to facilitate wound secretion flow, and as such may contain holes of various diameter, and, according to the indication of use, may have different dimensions.

The synthetic polymer layer improves the mechanical stability and strength of the natural polymer layer, the handling of the composite dressing product, and markedly improves protection of the wound against exogenous influences, such as bacteria, loss of fluids, drying, hyperhydration, temperature changes, and physical injury.

The natural polymer layer is physically adhered to the synthetic polymer foam layer by the adhesion that results from joining the natural fibers with the porous surface of the synthetic foam. This joinder is a form of physical/mechanical adhesion with the synthetic polymer foam resulting from the mechanical anchoring of the natural fibers that penetrate into the pores on the surface of the foam and that interlock within the porous surfaces. This physical-mechanical adhesion is most preferred, and avoids any need for the presence of additional adhesive materials. In this regard, a most preferred aspect of the present invention is the absence of chemical bonding between the natural and synthetic foam layers. Furthermore, the physical adhesive bond between the layers is most preferred for the ultimate use and performance of the present composite dressing. In this among other respects, the present composite distinguishes over the composite dressings in the prior art.

The present non-occlusive dressing may be packaged, sterilized and is ready to use without any pretreatment such as washing. The packaging of the present composite dressing is preferably substantially free of liquids, the only moisture being the residual moisture contained in the natural polymer layer after forming the solid sponge or membrane layer. The composite maintains its integrity by virtue of the strong physical adhesion between the natural and synthetic foam layers in the absence of fluids. The physical adherence is substantially weakened in the presence of significant moisture, such as when the composite is applied to a wound site. The present composite is preferably capable of layer separation provided that said natural layer is in contact with fluids for a sufficient time for said natural layer to be moistened. After being applied to the wound (according to the indication and medical intention), the natural polymer is moistened by blood and/or wound fluids, degraded and/or restructured due to biologically active substances and cells in-growing from the wound bed and wound borders. These processes lead to the gradual detachment or separation of the natural polymer layer from the synthetic polymer foam. When the synthetic layer is ready to be gently removed from the wound site without causing any substantial physical injury to the wound site, the natural polymer may be, at least partially, incorporated into the wound, and so directly participates in the healing process.

The synthetic silicone foam polymer mechanically stabilizes the natural polymer and forms a non-adhesive cover surface of the composite. This synthetic polymer surface is, at least partially, permeable to air and moisture, which permeability may be controlled by the present manufacturing process and the manufacture of the synthetic foam itself. The synthetic polymer can be easily removed from the surface of the wound due to the gradual separation of the natural polymer during the healing process as described above. Due to the open-pore and non adhesive structure of the synthetic polymer used in the present invention, the disadvantages of the prior synthetic wound dressings, including occlusion and insufficient exchange of air and fluids, as well as possible in-growth of the dressing into the wound bed, are avoided.

A most preferred embodiment of the non-occlusive composite includes a collagen sponge layer that is about 0.05 mm to about 5 mm thick and has a density of from about 5 mg/cm3 to about 750 mg/cm3. A further special embodiment of the preferred composite includes said collagen sponge layer that is about 0.05 mm to about 0.6 mm thick, has a density of about 200 mg/cm$^3$ to about 600 mg/cm3, and is capable of absorbing fluids in amounts of up to about 10 to about 30 times the weight of said sponge layer. A further most preferred embodiment of the present composite includes said collagen sponge layer that is capable of absorbing said fluids in less than about 30 seconds.

Another preferred aspect of the present invention is the process for the preparation of the non-occlusive composite wound dressing, which process comprises contacting a synthetic polymer foam porous surface with a solution and/or suspension of collagen fibers in a medium; and removing said medium from said collagen fibers under conditions that result in said fibers penetrating into pores of said surface and that form a dried composite of said synthetic polymer foam adhered physically to a layer of said collagen fiber.

The use of collagen dispersions for manufacturing collagen-based products is known; see for example, U.S. Pat. No. 4,060,081 or U.S. Pat. No. 4,925,924. The medium preferably used according to the invention is water, the pH of which is preferably weakly acidic. The concentration of the collagen fiber in the medium is preferably less than 4 wt percent, and more preferably less than 3 weight percent. The dispersion may also contain co-solvents that are easily volatile, for example, ethanol, and/or an inert gas and/or ice crystals.

The connection between the synthetic polymer, preferably a silicone foam, and the natural polymer, preferably a collagen, may be established as follows: an appropriate amount of a dispersion or solution of the natural polymer is poured into appropriate forms (e.g. dishes of various sizes and dimensions); a foam of a synthetic polymer (preferably an open-pore silicone foam which can be manufactured, for example, according to DE-A 195 42 687 and DE-A 197 29 227) is then placed on the surface of such dispersion (solution) layer. Particles (or fibers) of the natural polymer penetrate (due to differences in osmolarity and viscosity of both products) into the pores of the synthetic polymer foam. After removal of the medium (for example, by means of drying) both structures interlock so as to form a connection of a mechanical-physical nature. Pertinent drying processes stabilize the porous structure of the natural polymer.

Drying methods may comprise of freeze-drying or air-drying. Depending on the type of drying method used, the natural polymer may be formed as a sponge or as a membrane (fascia). The porosity of the natural polymer—in the form of a sponge—can be adjusted preferably by varying the drying process parameters, the natural polymer concentration, by adding salts, preferably sodium, calcium or potassium salts, or by adding other biologically acceptable solutions and/or substances. The ordinary skilled artisan knows the conditions for such modifications.

Alternatively, the dispersion or solution of the natural polymer, which is preferably an aqueous dispersion of collagen fibers, may be applied onto the wound bed-directed surface of the synthetic polymer foam, which is preferably a silicone elastomer foam, by pouring, and evenly spreading, the dispersion onto the foam surface. A preferred means for applying and spreading the dispersion is by means of a ductor blade. The concentration of the applied dispersion or solution (in grams of dispersed material per cm$^2$ of foam surface) can be vary over a broad range, and depend on the type of dispersion, the type and porosity of the synthetic polymer foam material, and the method to remove the medium.

For example, in the case of using commercially available open-pore silicone foams, 3-Si-Wundauflage®, the use of a 0.3 to 4.0 wt,-% collagen dispersion in water has proven successful.

A most preferred aspect of the present process is where the medium is removed from the dispersion under freeze-drying conditions that result in the formation of a porous collagen fiber sponge layer.

Another most preferred aspect of the present process is where the medium is removed from the dispersion under conditions that produce a transparent collagen fiber layer membrane.

The methods to remove the medium from the natural polymer dispersion or solution are known to the person skilled in the art. For example, the dispersion may be allowed to dry out under reduced pressure and/or increased temperature, yielding tightly adhering sponges or films of natural polymer on the surface of the foam of synthetic polymer. Natural polymer sponge layers that adhere to the foam may be obtained by contacting a, preferably aqueous, dispersion of natural polymer with the porous surface of the synthetic polymer foam so that these products combine physically and mechanically by incorporation of natural polymer particles or fibers into the synthetic polymer. The medium, which may also contain pore-forming substances, is then removed, preferably by freeze-drying. To increase the mechanical strength and/or the stability of the natural polymer, the final product may further be treated hydrothermally by heating under controlled humidity, or dehydrothermally by heating under reduced pressure.

A special embodiment of the present process further comprises the application of pressure and heat to said composite to compress the natural polymer layer and increase the absorption capacity of the natural polymer layer. The application of heat and pressure for as little as 0.5 seconds to about 30 seconds, and most preferably for about 10 seconds, at a pressure of about from about 0.1 to about 1000 kg/cm$^2$, preferably about 5 to about 25 kg/cm$^2$, and more preferably from about 5 to about 10 kg/cm2, is capable of increasing the density of said collagen sponge layer by about 8 to about 100 times its original density. Such treatment is capable of increasing the fluid absorption capacity of the natural layer and increasing the speed of such absorption, thereby enhancing the hemostatic function of the preferred embodiment of the present invention.

The present process further comprises the packaging of said dried composite; and the sterilizing of said dried composite. In a preferred embodiment the composite dressing of the invention, is packed in a standard suitable packaging and end-sterilized by ethylene oxide gassing, gamma radiation, electron beam radiation or by any other suitable sterilization method.

The present invention is exemplified by the following examples.

EXAMPLES

Example 1
Preparation of a Collagen Sponge/Silicone Foam Composite 50 ml of a 0.56% aqueous collagen dispersion (manufactured by SYNTACOLL AG, Herisau, Switzerland) are poured into an appropriate dish (e.g. 10×10 cm) at room temperature. A 70×100 mm open-pore silicone foam (Silcotech AG, Stein am Rhein, Switzerland, known as 3-Si-Wund-auflage®) is placed on the top of the dispersion.

The junction between the bioinert silicone foam and the collagen is formed by removing water, which serves as a medium for the natural polymer, by subjecting this arrangement to an air stream and/or controlled negative pressure which allows the natural polymer to dry out.

Described in detail, the natural polymer/synthetic polymer arrangement (i.e. collagen dispersion covered by an open-porous silicon foam, see above) is first continuously frozen in a freezing chamber to about −40° C. using a defined temperature gradient, i.e., about 10° C. per hour. This allows formation of ice crystals of only preferred and defined dimensions. Thereupon, a negative pressure of about 0.1 mbar is generated in the freezing chamber. The freezing chamber is aerated thereby so as to guarantee a continuous air stream. These conditions ensure controlled sublimation of the medium. At the end of the freezing/drying process the chamber is heated stepwise up to room temperature. This method is known for preparation of collagen sponges, and can be performed, for example, in an industrial freeze-drier.

This manufacturing process leads to a collagen/silicone composite, wherein the collagen has the structure of a sponge having desired porosity. The physical properties of the silicone foam are not affected thereby. Since the collagen dispersion penetrates into the pores of the silicone foam, both structures are interlocked on a mechanical-physical basis.

Example 2
Preparation of a Collagen Fascia/Silicone Foam Composite

For obtaining a membrane (fascia) of a natural polymer (preferably collagen), adhering to a bioinert foam (prepared from a synthetic polymer, preferably silicone) the water serving as the medium of the natural polymer dispersion (e.g. 0.8 wt.-% collagen dispersion) is removed by drying the latter at room temperature and under permanent and controlled air stream without having been previously frozen and/or subjected to the negative pressure. The medium completely sublimes thereby. This leads to a collagen/silicone composite, wherein the collagen has the structure of a transparent membrane.

The process of preparing collagen membranes is known and can be carried out without problems in an adequately aerated and heated chamber.

Example 3
Preparation of a Collagen Sponge/Silicone Foam Composite

The 70×100 mm, open-porous synthetic polymer (e.g. silicon foam known as 3-SiWund-auflage® and manufactured by Silcotech AG, Stein am Rhein, Switzerland) is placed on the bottom of an appropriate dish (e.g. 10×10 cm) at room temperature. 50 ml of a 0.56% dispersion of a natural polymer (e.g. collagen dispersion) in water (manufactured by SYNTACOLL AG, Herisau, Switzerland) are poured onto this open-pore foam of a synthetic polymer and spread evenly by means of a ductor blade. The junction between the bioinert silicone foam and the collagen is formed by removing water, which serves as a medium for the natural polymer, by subjecting this arrangement to an air stream and/or controlled negative pressure which allows the natural polymer to dry out.

Described in detail, the construct contained from an open-pore silicon foam with the collagen dispersion on the top is first continuously frozen in a freezing chamber to about −40° C. using a defined temperature gradient, i.e., about 10° C. per hour. This allows formation of ice crystals of only preferred and defined dimensions. Thereupon, a negative pressure of about 0.1 mbar is generated in the freezing chamber. The freezing chamber is aerated thereby so as to guarantee a continuous air stream. These conditions ensure controlled sublimation of the medium. At the end of the freezing/drying process the chamber is heated stepwise up to room temperature. This method is known for preparation of collagen sponges, and can be performed, for example, in an industrial freeze-drier.

Said manufacturing process yields a collagen/silicone composite, wherein the collagen has the structure of a sponge having the desired porosity. The physical properties of the silicone foam are not affected thereby. By the collagen dispersion penetrating into the pores of the silicone foam both structures are interlocked on a mechanical/physical basis.

The finished products prepared according to the examples are packed and sterilized by known and proven methods; with regard to sterilization, for example, gassing with ethylene oxide or sterilization with ionizing rays (e.g. gamma irradiation or electron beam) are carried out.

We claim:

1. A non-occlusive composite wound dressing comprising (1) a natural polymer would-healing layer comprised of isolated polymer fibers consisting essentially of helical collagen fibers, and (2) an at least partially air- and water vapor-permeable, non-biodegradable, bio-inert and fully polymerized synthetic polymer foam layer having at least one pore-containing surface contacting said natural layer and adhered to said natural layer by the physical interlocking of said polymer fibers with said pore-containing surface, wherein said natural and synthetic foam layers are not chemically bonded to each other and free of adhesive materials.

2. A non-occlusive dressing according to claim 1, wherein said non-biodegradable synthetic polymer foam layer is selected from the group consisting of silicone, polyurethane and polyvinyl alcohol.

3. A non-occlusive dressing according to claim 2, wherein said non-biodegradable synthetic polymer foam layer is a silicone polymer.

4. A process for the preparation of a non-occlusive composite wound dressing comprising:

(a) contacting a synthetic polymer foam surface comprising an open pore structure, with a solution or suspension of isolated natural polymer fibers in a medium consisting essentially of water; and (b) removing said medium from said fibers under conditions that result in said fibers penetrating into said pores and that form a dried composite of said synthetic polymer foam adhered physically to a layer of natural polymer fiber.

* * * * *

UNITED STATES PATENT AND TRADEMARK OFFICE
CERTIFICATE OF CORRECTION

PATENT NO. : 6,855,860 B2
DATED : February 15, 2005
INVENTOR(S) : Ruszczak et al.

It is certified that error appears in the above-identified patent and that said Letters Patent is hereby corrected as shown below:

<u>Title page,</u>
Item [73], Assignee, please replace "Syntagoll AG" with -- Syntacoll AG --

Signed and Sealed this

Seventeenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,855,860 B2
DATED : February 15, 2005
INVENTOR(S) : Ruszczak et al.

It is certified that error appears in the above-identified patent and that said Letters Patent is hereby corrected as shown below:

<u>Title page,</u>
Item [75], Inventors, add the following:
-- Rolf Siegel, Wurzburg, Germany
   Michael Stoltz, Munchen, Germany --.

Signed and Sealed this

Twenty-fifth Day of April, 2006

JON W. DUDAS
*Director of the United States Patent and Trademark Office*